United States Patent
Yoo et al.

(10) Patent No.: US 9,366,670 B2
(45) Date of Patent: Jun. 14, 2016

(54) POLYMER INCLUDING GROUP HAVING AT LEAST TWO HYDROXYLS OR ZWITTERIONIC GROUP AND USE THEREOF

(75) Inventors: Chang-eun Yoo, Seoul (KR); Ga-hee Kim, Yongin-si (KR); Hyun-ju Kang, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 911 days.

(21) Appl. No.: 13/541,378

(22) Filed: Jul. 3, 2012

(65) Prior Publication Data

US 2013/0011931 A1 Jan. 10, 2013

(30) Foreign Application Priority Data

Jul. 4, 2011 (KR) .................. 10-2011-0066158
Nov. 8, 2011 (KR) .................. 10-2011-0115926

(51) Int. Cl.
| | | |
|---|---|---|
| *G06F 19/00* | (2011.01) | |
| *G01N 33/543* | (2006.01) | |
| *C08F 8/30* | (2006.01) | |
| *C08F 220/26* | (2006.01) | |
| *C08F 220/06* | (2006.01) | |

(52) U.S. Cl.
CPC .......... *G01N 33/54353* (2013.01); *C08F 8/30* (2013.01); *C08F 220/06* (2013.01); *C08F 220/26* (2013.01); *Y10T 436/255* (2015.01)

(58) Field of Classification Search
CPC ........ C08F 8/30; B08F 220/06; B08F 220/26; G01N 33/54353; Y10T 436/255
See application file for complete search history.

(56) References Cited

U.S. PATENT DOCUMENTS

| 6,017,732 A * | 1/2000 | Jespers et al. ............... 435/69.6 |
| 2005/0064192 A1 | 3/2005 | Jiang et al. |
| 2006/0183863 A1 | 8/2006 | Huang et al. |
| 2008/0176761 A1 | 7/2008 | Menchen et al. |
| 2011/0306148 A1 * | 12/2011 | Lele et al. .................... 436/501 |
| 2012/0070848 A1 * | 3/2012 | Rak et al. .................... 435/7.23 |

FOREIGN PATENT DOCUMENTS

| JP | 07-198721 A | 8/1995 |
| WO | WO 2006/007207 A2 | 1/2006 |
| WO | WO 2011/159548 A1 | 12/2011 |
| WO | WO 2013/110828 A1 | 8/2013 |

OTHER PUBLICATIONS

European Patent Office, Examination Report in European Patent Application No. 12174976.6, Nov. 17, 2014, 7 pp.
Thümmler et al., "Surfactant-Free Poly(styrene-co-glycidyl methacrylate) Particles with Surface-Bound Antibodies for Activation and Proliferation of Human T Cells," *Bioconjugate Chem.*, 21: 867-874 (2010).
Wattendorf et al., "PEGylation as a Tool for the Biomedical Engineering of Surface Modified Microparticles," *J. of Pharmaceutical Sciences*, 97(11): 4655-4669 (2008).
Extended European Search Report by the European Patent Office in European Patent Application No. 12174976.6, mailed on Nov. 26, 2012.
Holmlin et al., Zwitterionic SAMs that Resist Nonspecific Adsorption of Protein from Aqueous Buffer, *Langmuir*, 17(9): 2841-2850 (2001).
European Patent Office, Examination Report in European Patent Application No. 12174976.6, Mar. 14, 2014, 8 pp.
Quan et al., "Resurveying the Tris Buffer Solution: The Specific Interaction Between Tris (Hydroxymethyl) Aminomethane and Lysozyme," *Analytical Biochemistry*, 2008, 378: 144-150.
Ostuni, Emanuele et al., "A Survey of Structure-Property Relationships of Surfaces that Resist the Adsorption of Protein," *Langmuire*, 17, pp. 5605-5620 (2001).
Chang, Yung et al., "A Highly Stable Nonbiofouling Surface with Well-Packed Grafted Zwitterionic Polysulfobetaine for Plasma Protein Repulsion," *Langmuire*, 24, pp. 5453-5458 (2008).
Sakaki, Shujirou et al, "Water-Soluble 2-Methacryloyloxyethyl Phosphorylcholine Copolymer as a Novel Synthetic Blocking Reagent in Immunoassay System," *Polymer Journal*, 32, pp. 637-641 (2000).

* cited by examiner

*Primary Examiner* — Christopher A Hixson
(74) *Attorney, Agent, or Firm* — Leydig, Voit & Mayer, Ltd.

(57) ABSTRACT

A solid support comprising a polymer that includes a group having at least two hydroxyls or a zwitterionic group and a method of using the same.

10 Claims, 2 Drawing Sheets

POLYMER INCLUDING GROUP HAVING AT LEAST TWO HYDROXYLS OR ZWITTERIONIC GROUP AND USE THEREOF

CROSS-REFERENCE TO RELATED APPLICATIONS

This application claims the benefit of Korean Patent Application No. 10-2011-0066158, filed on Jul. 4, 2011, and Korean Patent Application No. 10-2011-0115926, filed on Nov. 8, 2011, in the Korean Intellectual Property Office, the disclosures of which are incorporated herein in their entirety by reference.

BACKGROUND

1. Field

The present disclosure relates to polymers containing a group having at least two hydroxyls or a zwitterionic group and methods of using the same.

2. Description of the Related Art

Methods of binding biomolecules to a support or methods of separating biomolecules therefrom are known. For example, protein separation devices including a ligand protein immobilized on a support are known. However, when such methods, which are used to separate protein that is specifically bound to a ligand, are used, non-specific binding of biomolecules to a support needs to be prevented to enhance binding and detection efficiencies.

Traditionally, to decrease a non-specific binding between a support and protein, a method of blocking a site of a support at which a non-specific binding occurs by using a blocking agent such as bovine serum albumin (BSA) is known.

Acrylate polymers belong to a group of polymers. Acrylate monomers that may be used in acrylate polymers include acrylic acids, methyl methacrylates, and acrylonitriles. Examples of the acrylate polymers include polyacrylate, polymethacrylate, and polyacrylonitrile. In addition, acrylate polymers may be acrylic elastomers, acrylic fibers, acrylic paints, or acrylic resins.

However, polymers containing a group having at least two hydroxyls or a zwitterionic group that exhibit low non-specific binding with biomolecules are still not known.

SUMMARY

Provided are polymers containing a group having at least two hydroxyls or a zwitterionic group.

Provided are methods of binding biomolecules to the polymers.

Provided are methods of detecting biomolecules in a sample by using the polymers.

Additional aspects will be set forth in part in the description which follows and, in part, will be apparent from the description, or may be learned by practice of the presented embodiments.

According to an aspect of the present invention, there is provided a solid support on which at least one polymer including at least one repeating unit of Formula M1 and at least one repeating unit of Formula M2 is immobilized:

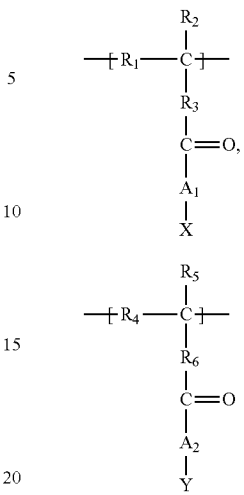

wherein $R_1$, $R_3$, $R_4$, and $R_6$ are each independently a bond or a substituted or unsubstituted $C_{1-6}$ alkylene group, $R_2$ and $R_5$ are each independently hydrogen, halo, or a substituted or unsubstituted $C_{1-6}$ alkyl group, and a substituent of the substituted $R_1$, $R_2$, $R_3$, $R_4$, $R_5$, and $R_6$ may be halo or $C_{1-3}$ alkyl $A_1$ and $A_2$ are each independently —NH—, —O—, or —O—(CO)—, and X and Y are each independently —H, a group having at least two hydroxyls, a zwitterionic group, PEG (polyethylene glycol) group, or a material specifically binding to one or more biomolecules.

Also provided is a method of binding biomolecules in a sample to the solid support, which includes contacting a solid support with biomolecules in a sample to form a biomolecule-solid support composite.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
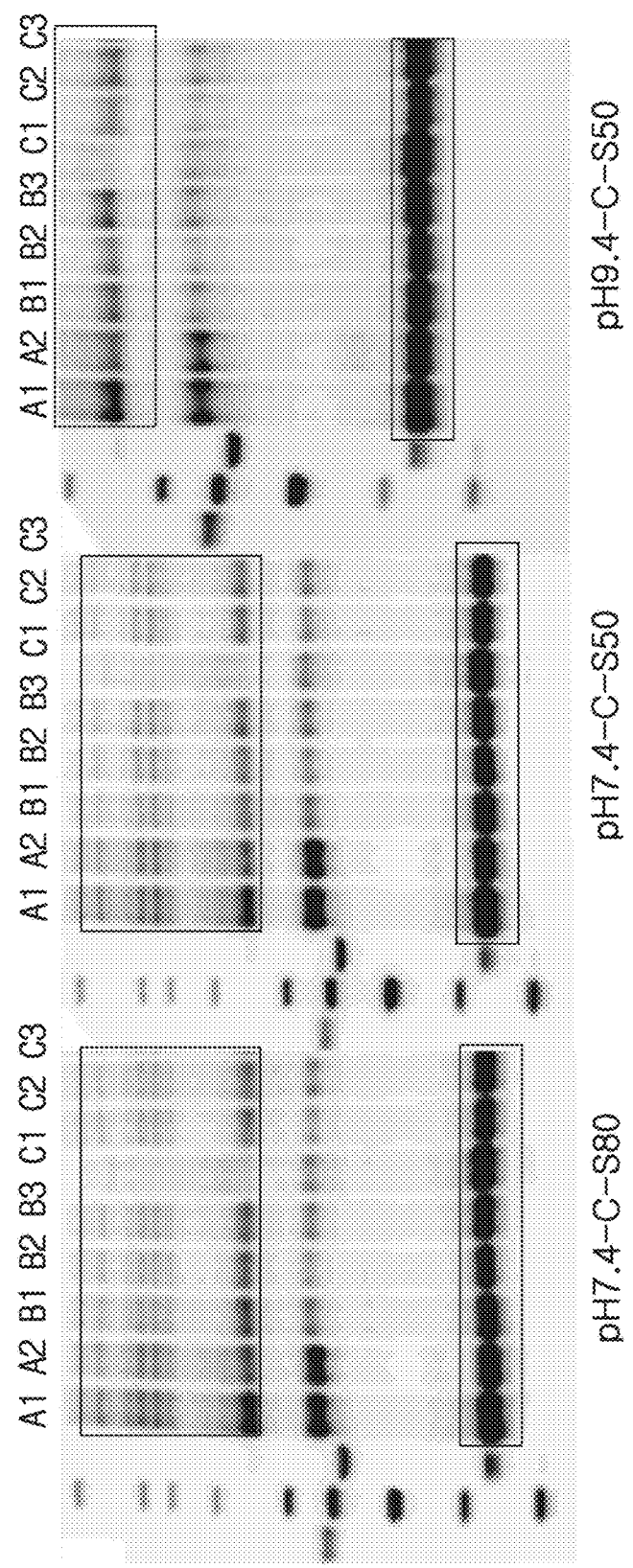
FIG. 1 illustrates western blotting results of a polymer with a serum-containing cell lysate bound thereto, according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

According to an embodiment of the present invention, there is provided a solid support on which at least one polymer is immobilized, wherein the polymer includes at least one repeating unit of Formula M1 below and at least one repeating unit of Formula M2 below:

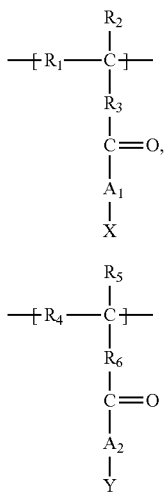

(M1)

(M2)

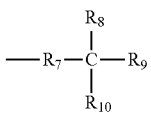

<Formula 1>

According to Formula M1 and M2, $R_1$, $R_3$, $R_4$, and $R_6$ are each independently a bond or a substituted or unsubstituted $C_{1-6}$ alkylene group, $R_2$ and $R_5$ are each independently hydrogen, halo, or a substituted or unsubstituted $C_{1-6}$ alkyl group. When any one or more of $R_1$-$R_6$ is an alkylene, the alkyl may, according to certain embodiments may be substituted with halo or a $C_{1-3}$ alkyl group.

$A_1$ and $A_2$ are each independently —NH—, —O—, or —O—(CO)—, and

X and Y are each independently selected from the group consisting of —H, a group having at least two hydroxyls, a zwitterionic group, PEG, and a material specifically binding to biomolecules.

In Formulae M1 and M2, $R_1$, $R_3$, $R_4$, and $R_6$ may be each independently a bond, for example, a single bond, or a substituted or unsubstituted $C_{1-6}$ alkyl group, for example, methyl, ethyl, propyl, isopropyl, butyl, sec-butyl, tert-butyl, pentyl, hexyl, or the like; $R_2$ and $R_5$ may be each independently hydrogen, halo, or a substituted or unsubstituted $C_{1-6}$ alkyl group, for example, methyl, ethyl, propyl, isopropyl, butyl, sec-butyl, tert-butyl, pentyl, hexyl, or the like; and any of $R_1$, $R_2$, $R_3$, $R_4$, $R_5$, and $R_6$ may be further substituted with halo or a $C_{1-3}$ alkyl group, for example, methyl, ethyl, propyl, or isopropyl. For example, in Formulae M1 and M2, each of $R_1$ and $R_4$ may be —$CH_2$—, each of $R_3$ and $R_6$ may be a single bond, and each of $R_2$ and $R_5$ may be —H.

In the polymer, the number of the repeating units of Formula M1 and/or M2 may be 1 to 300, for example, 1 to 250, 1 to 200, 1 to 180, 10 to 300, 10 to 250, 10 to 200, 10 to 180, 30 to 300, 30 to 250, 30 to 200, 30 to 180, 50 to 300, 50 to 250, 50 to 200, 50 to 180, 70 to 300, 90 to 250, 100 to 200, or 100 to 180, and the number of the repeating units of Formula M2 may be 1 to 300, for example, 1 to 250, 1 to 200, 1 to 180, 10 to 300, 10 to 250, 10 to 200, 10 to 180, 30 to 300, 30 to 250, 30 to 200, 30 to 180, 50 to 300, 50 to 250, 50 to 200, 50 to 180, 70 to 300, 90 to 250, 100 to 200, or 100 to 180. Any sub-range of the foregoing is specifically contemplated (e.g., 2 or more repeating units, 5 or more repeating units, etc., as well as 300 or fewer repeating units, 250 or fewer repeating units, 200 or fewer repeating units, etc.).

The group having at least two hydroxyls may be represented by Formula 1 below:

wherein $R_7$ may be a single bond, a substituted or unsubstituted $C_{1-6}$ alkylene group, a substituted or unsubstituted $C_{6-12}$ arylene group, a substituted or unsubstituted $C_{1-6}$ alkyl-$C_{6-12}$ arylene group, or a substituted or unsubstituted $C_{6-12}$ aryl-$C_{1-6}$ alkylene group; $R_8$, $R_9$, and $R_{10}$ may be each independently H, halo, or a substituted or unsubstituted $C_{1-6}$ hydroxyalkyl group, wherein at least two of $R_8$, $R_9$, and $R_{10}$ are each independently a substituted or unsubstituted $C_{1-6}$ hydroxyalkyl group; and any of $R_7$, $R_8$, $R_9$, and $R_{10}$ may be optionally substituted with halo or $C_{1-3}$ alkyl. For example, the $C_{1-6}$ alkylene group of $R_7$ may be methylene, ethylene, propylene, isopropylene, butylene, sec-butylene, tert-butylene, pentylene, or hexylene. The $C_{6-12}$ arylene group of $R_7$ may be phenylene or naphthylene. The $C_{1-6}$ hydroxyalkyl group of each of $R_8$, $R_9$, and $R_{10}$ may be a hydroxymethyl group, a hydroxyethyl group, a hydroxypropyl group, a hydroxyisopropyl group, a hydroxybutyl group, a hydroxyl-sec-butyl group, a hydroxyl-tert-butyl group, a hydroxypentyl group, or a hydroxyhexyl group. Also, any one or more of $R_7$, $R_8$, $R_9$, and $R_{10}$, may optionally be further substituted with a halo or $C_{1-3}$ alkyl, such as methyl, ethyl, propyl, or isopropyl.

The group having at least two hydroxyls may be represented by Formula 1 where $R_7$ is a single bond and each of $R_8$, $R_9$, and $R_{10}$ is independently hydroxyalkyl. For example, in Formula 1, $R_7$ may be a single bond and $R_8$, $R_9$, and $R_{10}$ may be each independently —$CH_3OH$.

The zwitterionic group may be represented by Formula 2 below:

$$-L_1-A_3-L_2-A_4 \qquad \text{<Formula 2>}$$

wherein $L_1$ and $L_2$ may be each independently a substituted or unsubstituted $C_{1-100}$ alkylene group, a substituted or unsubstituted $C_{6-100}$ arylene group, a substituted or unsubstituted $C_{1-50}$ alkyl-$C_{6-50}$ arylene group, or a substituted or unsubstituted $C_{6-50}$ aryl-$C_{1-50}$ alkylene group, and $A_3$ and $A_4$ are both ionic groups (i.e., each independently comprises a group having a cation or an anion. In this regard, $A_3$ and $A_4$ may have opposite charged ions. For instance, $A_3$ may be a cationic group, and $A_4$ may be an anionic group, or vice versa ($A_4$ may be a cationic group, and $A_3$ may be an anionic group). The group having a cation may be, for example, a substituted or unsubstituted amino group. The group having an anion may be, for example, a substituted or unsubstituted phosphate group or phosphoryl group, a substituted or unsubstituted sulfate group or sulfuryl group, or a substituted or unsubstituted sulfonate group or sulfonyl group. A substituent of the substituted groups may be, for instance, a halo or a $C_{1-3}$ alkyl group.

The zwitterionic group may be represented by Formula 3 or 4 below:

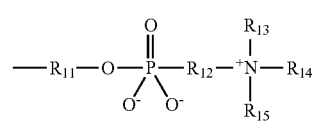

<Formula 3>

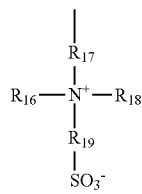
<Formula 4> wherein $R_{11}$, $R_{12}$, $R_{17}$, and $R_{19}$ may be each independently a substituted or unsubstituted $C_{1-6}$ alkylene group, a substituted or unsubstituted $C_{6-12}$ arylene group, a substituted or unsubstituted $C_{1-6}$ alkyl-$C_{6-12}$ arylene group, or a substituted or unsubstituted $C_{6-12}$ aryl-$C_{1-6}$ alkylene group, and $R_{13}$, $R_{14}$, $R_{15}$, $R_{16}$, and $R_{18}$ may be each independently H or a substituted or unsubstituted $C_{1-6}$ alkyl group. A substituent of the substituted group may be, for example, halo or $C_{1-3}$ alkyl.

By way of further illustration, the $C_{1-6}$ alkylene group of each of $R_{11}$, $R_{12}$, $R_{17}$, and $R_{19}$ may be methylene, ethylene, propylene, isopropylene, butylene, sec-butylene, tert-butylene, pentylene, or hexylene. The $C_{6-12}$ arylene group of each of $R_{11}$, $R_{12}$, $R_{17}$, and $R_{19}$ may be phenylene or naphthylene. The $C_{1-6}$ alkyl group of each of $R_{13}$, $R_{14}$, $R_{15}$, $R_{16}$, and $R_{18}$ may be methyl, ethyl, propyl, isopropyl, butyl, sec-butyl, tert-butyl, pentyl, or hexyl. The substituent of the substituted $C_{1-6}$ alkyl group may be methyl, ethyl, propyl, or isopropyl.

As a further example, in Formula 3 above, $R_{11}$ may be phenylene or methylene, $R_{12}$ may be ethylene, and $R_{13}$, $R_{14}$, and $R_{15}$ may be each independently methyl.

As another example, in Formula 4 above, $R_{17}$ may be ethyl, $R_{19}$ may be ethyl, and each of $R_{16}$ and $R_{18}$ may be methyl.

PEG may have a molecular weight of 1,000 Da to 15,000 Da.

The solid support may be of any shape. For example, the solid support may be in the form of a bead, a plate, or a well. The solid support (or surface thereof) may be formed of a material that is not non-specifically binding to biomolecules or exhibits low binding with biomolecules. For example, the solid support (or surface thereof) may comprise polyethylene, polypropylene, polybutylene, polyvinyl chloride, polystyrene, or a combination, mixture, or copolymer thereof. A cross-sectional length of the solid support may be 100 nm or greater. For example, the solid support may have at least one cross-sectional length of 1,000 nm, 10 μm, 100 μm, or 1,000 μm or greater. The at least one cross-sectional length of the solid support may be in the range of about 100 nm to about 1,000 μm, about 1,000 nm to about 1,000 μm, about 10 μm to about 1,000 μm, about 100 μm to about 1,000 μm, about 1 μm to about 1,000 μm, about 2 μm to about 1,000 μm, about 1,000 nm to about 100 μm, about 1 μm to about 10 μm, about 1 μm to about 5 μm, or about 1 μm to about 7 μm.

The polymer may be a plurality of polymers that are bonded to a solid support, such as to a surface of the solid support. For example, 2, 5, 10, 20, 50, 100, 200, 500, 1000, 2000, 5000, or 10,000 polymers may be bound to a solid support. For example, the number of polymers bonded to a solid support may be in the range of about 2 to about 10,000, about 5 to about 10,000, about 10 to about 10,000, about 20 to about 10,000, about 50 to about 10,000, about 100 to about 10,000, about 200 to about 10,000, about 500 to about 10,000, about 1,000 to about 10,000, about 2,000 to about 10,000, about 5,000 to about 10,000, about 2 to about 5,000, about 5 to about 5,000, about 10 to about 5,000, about 20 to about 5,000, about 50 to about 5,000, about 100 to about 5,000, about 200 to about 5,000, about 500 to about 5,000, about 1,000 to about 5,000, about 2,000 to about 5,000, about 2 to about 2,000, about 5 to about 2,000, about 10 to about 2,000, about 20 to about 2,000, about 50 to about 2,000, about 100 to about 2,000, about 200 to about 2,000, about 500 to about 2,000, or about 1,000 to about 2,000.

According to one embodiment, the polymer comprises a group that specifically binds one or more biomolecules, such as proteins, nucleic acids, sugars, or a combination thereof. For example, the biomolecules may be protein. The term "protein" used herein refers to molecules that entirely or partially include polymers in which natural or non-natural amino acids are linked by amide bonds. The protein also includes a protein analog such as peptide nucleic acid (PNA). The term "analog" used herein is interpreted to include, as a natural protein where amino acid side chains are exposed on the molecule's surface, molecules having groups corresponding to natural or non-natural amino acid side chains which are linked to the backbone of molecules. The protein may be a natural or non-natural protein. The protein may exist in or on a microvesicle. For example, the protein may exist on a membrane surface of the microvesicle or inside the microvesicle. The term "microvesicle" used herein refers to fragments of a cell membrane and is also referred to as exosome, a circulating microvesicle, or microparticles. The microvesicle may have a cross-sectional length in the range of about 50 nm to about 1,000 nm.

Any material that specifically binds to biomolecules may be used. The material may include one or more proteins, nucleic acids, sugars, or combinations thereof. For example, the material may be an antibody, an antigen against an antibody, a receptor against a ligand, a ligand against a receptor, a substrate or inhibitor of an enzyme, or an enzyme against a substrate or inhibitor. In one embodiment, the material specifically binding to biomolecules may be an antibody to a protein that exists in or on a microvesicle, for example, on a surface of a microvesicle membrane.

The polymer may be synthesized by synthesizing a polymer including the repeating units of Formulae M1 and M2, for example, where $A_1$ and $A_2$ are each independently —O— and X and Y are each independently —H, i.e., repeating units having a carboxyl group or a blocked form thereof, and coupling the carboxyl group or the blocked form thereof with a group having at least two hydroxyls, a zwitterionic group, PEG, or a material specifically binding to biomolecules. The coupling reaction may be performed by a reaction with a functional group such as an amino group of molecules or an amino group introduced by functionalization. The polymer including the repeating units having a carboxyl group or a blocked form thereof may be poly(acrylic acid) (PAA) or poly(methacrylic acid) (PMAA). For example, the polymer may be synthesized by immobilizing on a solid support a polymer including the repeating units of Formulae M1 and M2 having a carboxyl group or a blocked form thereof and sequentially or simultaneously coupling the polymer with the groups represented by Formulae 1, 2, 3, 4, or a combination thereof. The immobilizing of the polymer on a solid support may be performed using a known method of immobilizing a polymer on a solid support having a reactive group. For example, the immobilizing process may be performed by reacting the polymer having a carbonyl group activated with carbodiimide with a solid support having a reactive amino group on its surface to immobilize the polymer on the solid support through an amide bond by the reaction between the amino group and the activated carbonyl group.

The coupling process may be performed as follows. First, carboxyl groups of the polymer including the repeating units of Formulae M1 and M2 having an activatable carboxyl group, for example, an acrylic polymer such as poly(acrylic acid) (PAA), poly(methacrylic acid) (PMAA), or poly(ethylacrylic acid) are activated with carbodiimide (e.g., 1-ethyl-3-(3-dimethylaminopropyl)carbodiimide (EDC)) and the activated carboxyl groups are coupled with an amino group existing on a surface of the solid support and at least one of the amino groups of the groups of Formulae 1, 2, 3, and 4, wherein the group of Formula 1 has an amino group functionalized with at least one hydroxyl site, for example, a hydroxyl group at the end.

In the polymer, 10% to 90% of the repeating units may have the material specifically binding to biomolecules. In addition, 10% to 90% of the repeating units may have a group selected from the group consisting of a group having at least two hydroxyls, a zwitterionic group, PEG, and combinations thereof. In the repeating units of the polymer, a molar ratio of the group specifically binding to biomolecules to the material selected from the group consisting of a group having at least two hydroxyls, a zwitterionic group, and PEG may be in the range of about 1:9 to about 9:1. The solid support may have at least one polymer immobilized thereon and at least one material specifically binding to biomolecules is immobilized on the at least one polymer and thus the material specifically binding to biomolecules may be immobilized at a high density on the solid support.

The polymer may have a group selected from the group consisting of a group having at least two hydroxyls and a zwitterionic group.

The polymer may include the repeating unit of Formula M1 where $A_1$ is —O— and X is H or the repeating unit of Formula M2 where $A_2$ is —O— and Y is H and the solid support may be bonded to the polymer via binding with a carboxyl group of the repeating unit of Formula M1 or M2.

The solid support may have at least one polymer immobilized thereon that includes the repeating units of Formulae M1 and M2 wherein, except for a portion of the polymer bonded to the solid support, $R_1$ and $R_4$ are each independently —CH$_2$—, $R_3$ and $R_6$ are each independently a single bond, $R_2$ and $R_5$ are each independently —H, $A_1$ and $A_2$ are each independently —NH—, and X and Y are each independently selected from the group consisting of —H, a group having at least two hydroxyls, a zwitterionic group, PEG, and a material specifically binding to biomolecules. In Formula 1 representing the group having at least two hydroxyls, $R_7$ may be a single bond and $R_8$, $R_9$, and $R_{10}$ may be each independently —CH$_2$OH. In Formula 3 representing the zwitterionic group, $R_{11}$ may be a phenyl methyl group, $R_{12}$ may be —(CH$_2$)$_2$—, and $R_{13}$, $R_{14}$, and $R_{15}$ may be each independently —CH$_3$. In Formula 4 representing the zwitterionic group, $R_{17}$ may be —(CH$_2$)$_3$—, $R_{16}$ and $R_{18}$ may be each independently —CH$_3$, and $R_{19}$ may be —(CH$_2$)$_3$—.

When the polymer-solid support composite is used, certain biomolecules may be specifically bound to the polymer-solid support composite without any significant degree of non-specific binding of biomolecules, e.g., protein being bound thereto. In other words, the solid support binds to some biomolecules (target biomolecules) to a greater degree than other biomolecules (non-target biomolecules).

According to another embodiment of the present invention, there is provided the polymer described above that is not bound to a solid support, as well as a method of preparing the polymer. A detailed description of the polymer is already provided.

According to another embodiment of the present invention, there is provided a method of binding biomolecules in a sample to a solid support, the method including contacting a solid support on which at least one polymer including at least one repeating unit selected from groups represented by Formula M1 below and at least one repeating unit selected from groups represented by Formula M2 below is immobilized with the biomolecules in a sample to form a biomolecule-solid support composite:

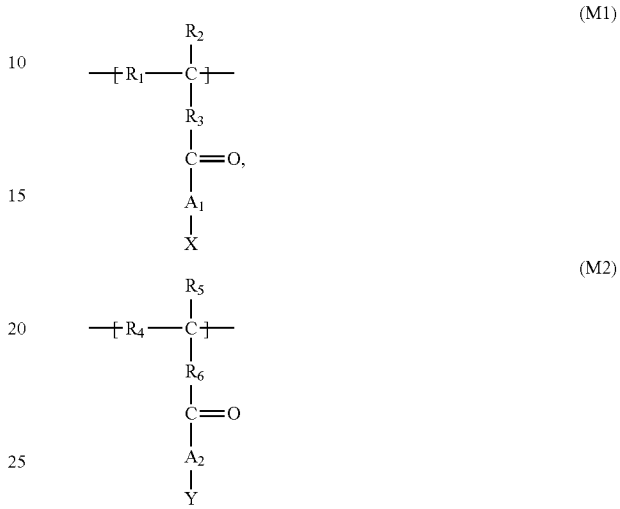

wherein $R_1$, $R_3$, $R_4$, and $R_6$ are each independently a bond or a substituted or unsubstituted $C_{1-6}$ alkylene group, $R_2$ and $R_5$ are each independently hydrogen, halo, or a substituted or unsubstituted $C_{1-6}$ alkyl group, and a substituent of the substituted $R_1$, $R_2$, $R_3$, $R_4$, $R_5$, and $R_6$ may be halo or $C_{1-3}$ alkyl, $A_1$ and $A_2$ are each independently —NH—, —O—, or —O—(CO)—, and X and Y are each independently selected from the group consisting of —H, a group having at least two hydroxyls, a zwitterionic group, PEG, and a material specifically binding to biomolecules. All aspects of the solid support used in the method are as previously described herein.

The contacting process may be performed under conditions where the material specifically binding to biomolecules of the polymer is bound to the biomolecules. For example, the contacting process may be performed in a liquid medium having pH, a salt concentration, and temperature that are suitable for binding between the material and the biomolecules. The liquid medium may be water or a buffer (e.g. a PBS buffer). The pH may be a physiological pH, for example, in the range of about 6.8 to about 7.0. For example, the temperature may be in the range of about 15° C. to about 40° C. for example, in the range of about 15° C. to about 37° C. These reaction conditions may be appropriately selected by one of ordinary skill in the art according to selected biomolecules and material specifically binding thereto.

A detailed description of the polymer and biomolecules used in the contacting process is already provided above in the description of the solid support. The sample may be a certain biomolecule-containing sample. The sample may be obtained from a living body or contain artificially synthesized biomolecules. For example, the sample may be a sample containing a microvesicle or a lysate thereof. The biomolecule-polymer composite may be formed by binding between an antibody and an antigen, between a ligand and a receptor, or between an enzyme and a substrate, an inhibitor or activator of an enzyme, or a coenzyme.

The method may further include washing the biomolecule-polymer composite after the contacting process. The washing process may be performed to remove materials non-specifically binding to the biomolecules and/or the polymer, with the binding of the composite being maintained. For example, the washing process may be performed by flowing over the biomolecule-polymer composite a liquid medium capable of removing the materials non-specifically binding to the biomolecules and/or the polymer, for example, water or a buffer (e.g., a PBS buffer), with the binding of the composite being maintained.

The method may further include eluting biomolecules from the biomolecule-polymer composite after the contacting process. The eluting process may be performed by flowing a liquid medium capable of removing the binding of the biomolecule-polymer composite over the biomolecule-polymer composite. The eluting process may be performed with given gradients of pH and/or salt concentration in the liquid medium. An eluent used in the eluting process may be a liquid medium that is appropriately given with gradients of pH and/or salt concentration according to selected biomolecules and material specifically binding thereto, for example, water or a buffer (e.g., a PBS buffer). These eluting conditions may be appropriately selected by one of ordinary skill in the art according to the selected biomolecules and material specifically binding thereto. For example, if protein is selected as the biomolecules and the material specifically binding thereto is an antibody, the eluting process may be performed using a well-known method in the art such as a method of separating an antigen, for example, protein by using an antibody-based affinity chromatography and the eluting conditions are obvious to one of ordinary skill in the art.

By using the method described above, specific biomolecules may be specifically bound to the polymer without binding of non-specific biomolecules, for example, protein thereto. Also, a material containing specific biomolecules, for example, a cell or a microvesicle may be specifically bound to the polymer by the specific binding between the specific biomolecules and the polymer.

By the method described above, specific biomolecules may be separated from a sample without binding of non-specific biomolecules. In addition, a material containing specific biomolecules, for example, a cell or a microvesicle may be specifically separated from a sample by specific binding between the specific biomolecules and the polymer and separation of the specific biomolecules therefrom.

The method may further include confirming whether biomolecules in the sample are bound to the polymer; and determining that, if the biomolecules are bound to the polymer, the biomolecules exist in the sample and that, if the biomolecules are not bound to the polymer, the biomolecules do not exist in the sample.

The method includes confirming whether the biomolecules in a sample are bound to the polymer. The confirming process may be performed by detecting whether or not the biomolecule-polymer composite exists. Also, the confirming process may be performed by eluting the biomolecules from the biomolecule-polymer composite. The detecting process may be performed using various well-known methods in the art such as a spectroscopic method, an electric method, or enzyme-linked immunosorbent assay (ELISA).

One or more embodiments of the present invention will now be described in more detail with reference to the following Examples. These Examples are for illustrative purposes only and are not intended to limit the scope of the invention.

Example 1

Preparation of Polymer and Binding of Biomolecules Thereto

1. Synthesis of Polymer

A poly(acrylic acid) (PAA) including the repeating units of Formulae M1 and M2 where X and Y are each independently —OH, A is —O—, $R_1$ and $R_4$ are each independently —CH$_2$—, $R_2$ and $R_5$ are each independently —H, and $R_3$ and $R_6$ are each independently a single bond (—) was prepared as a polymer and the polymer was bound to a surface of a solid support. Subsequently, a carboxyl group of PAA was activated with carbodiimide and the activated carboxyl group reacted with amino groups of the group of Formula 1, wherein the group of Formula 1 has an amino group functionalized with at least one hydroxyl site, for example, a hydroxyl group at the end; the group of Formula 2 or 3; and amino groups of biomolecules (e.g., protein) to immobilize the groups of Formula 1 and Formula 2 or 3 and biomolecules (e.g., protein) on the solid support. The solid support used was in the form of a bead. The preparation of the polymer will now be described in more detail.

(1) Binding of First Polymer Having Carboxyl Group to Magnetic Bead

Magnetic beads were used as the solid support. Dynabeads® M-270 Amine (available from Invitrogen) were used. Dynabeads® M-270 Amine are uniform, superparamagnetic beads composed of highly cross-linked polystyrene with magnetic material precipitated in pores evenly distributed throughout the beads. The beads are further coated with a hydrophilic layer of glycidyl ether which seals the iron oxide inside the beads, and the surface is activated with primary amino functional groups on a short hydrophilic linker.

The hydrophilic surface ensures low non-specific binding, excellent dispersion abilities, and easy handling of the beads in a wide variety of buffers. The beads are commercially available as an aqueous suspension at a concentration of $2 \times 10^9$ beads/ml (approximately 30 mg/ml). The diameter of the beads was 2.8 μm. Surface-reactive primary amino groups allow immobilization of ligands such as proteins, peptides, carbohydrates or other target specific molecules.

100 μl of Dynabeads® M-270 Amine (available from Invitrogen) were washed twice with 200 μl of 0.1M 2-(N-morpholino)ethanesulfonic acid (MES), 0.5 M NaCl, pH 6 buffer and then resuspended in 100 μl of the same buffer. 48 μl of a 1:10 diluted solution of a PAA solution (35% w/v in water, average molecular weight ($M_w$) of about 15,000 Da, catalog No.: 416037, available from Aldrich) and 236 μl of the buffer were mixed together and the resultant mixture was added to the resuspended bead solution and mixed well.

Next, 54 μl of a solution in which 75 mg/ml of 1-ethyl-3-(3-dimethylaminopropyl)carbodiimide (EDC) is dissolved in distilled water and 210 μl of a solution in which 15 mg/ml of N-hydroxysuccinimide (NHS) is dissolved in distilled water were added to the mixture and the resulting mixture was rotated for 1 hour. Subsequently, the mixture was washed twice with 400 μl of 0.5M NaCl buffer (pH 6.0) and resuspended in 400 μl of the same buffer. As a result, magnetic beads with PAA bound to the surfaces by an amide bond were obtained. The amide bond was formed by binding between a carbonyl group of PAA and primary amino groups of the magnetic beads.

(2) Binding Between Magnetic Beads with PAA Bound to the Surfaces and Protein G

The bead suspension prepared according to (1) was washed twice with 400 μl of 0.025 M MES buffer (pH 6.0). Subsequently, 236 μl of the 0.025 M MES buffer (pH 6.0), 54 μl of an EDC solution (75 mg EDC/ml in 0.025 M MES, pH 6.0 buffer), and 210 μl of an NHS solution (15 mg NHS/ml in 0.025 M MES, pH 6.0 buffer) were added to the resultant bead suspension and mixed together, and the resultant mixture was then rotated for 30 minutes.

The magnetic beads were washed twice with 400 μl of the 0.025 M MES buffer (pH 6.0) and resuspended in 400 μl of the 0.025 M MES buffer (pH 6.0). Then, 3 µl of a protein G solution (10 µg/µl) (available from Fluka, catalog No.: 08062) was added to the bead suspension and the resultant mixture was rotated for 1 hour.

As a result, magnetic beads having PAA with protein G bound thereto on their surfaces were obtained. In this regard, protein G may be bound to the magnetic beads via a carbonyl group of PAA.

According to the type of blockers to be used in the reaction product, each broker was added to the reaction product to couple the blocker with a backbone of the PAA. In particular, each of 28 µl of a Tris solution (100 µg/µl of tri(hydroxymethyl)aminomethane (Tris) in distilled water), 50 µl of a APC solution (100 µg/µl of 4-aminophenylmethylphosphorylcoline (APC) in distilled water), 300 µl of a SB solution (100 µg/µl of sulfobetaine (SB, $NH_2(CH_2)_3N^+(CH_3)_2(CH_2)_3SO_3^-$) in distilled water), and 300 µl of a PEG solution (20 µg/µl of polyethyleneglycol (PEG) (BlockMaster, JSR corporation: Mw=5,000 Da) in distilled water) was added to the reaction product and the mixture was rotated for 1 to 2 hours. Each reaction product was washed twice with 400 µl of 1× PBS (0.02% Tween 20) and washed twice with 400 µl of 1× PBS. In this regard, PEG whose terminal OH group is functionalized to an amino group was used.

(3) Binding Between Protein G and Antibody

Magnetic beads were separated from the bead suspension prepared according to (2) above by using a magnet and washed twice with 400 µl of 0.1M sodium acetate buffer (pH 5.0).

80 µl of anti-Rab5b antibody (available from SantaCruz, catalog No.: sc-598, 200 µl/ml) and 420 µl of 0.1M sodium acetate buffer (pH 5.0) were mixed together, the washed magnetic beads were added to the mixed solution, and the resultant mixture was rotated for 1 hour. The reaction product was washed twice with 400 µl of 1× PBS buffer (0.02% Tween 20), washed twice with 400 µl of 1× PBS buffer, and resuspended in 100 µl of 1× PBS buffer. Rab5b is a member of the RAS oncogene family. Rab protein is small GTPase involved in the regulation of membrane traffic. Rab5a is known to regulate transportation in early endocytosis. Rab5b and Rab5a are isoforms of Rab5 and Rab5b that shares all the characteristics needed to regulate endocytosis with Rab5a. Rab5b and Rab5c are co-localized with a transferrin receptor and Rab5a and accelerate fusion between in vitro early endosomes. Thus, when over-expressed in vivo, Rab5b and Rab5c accelerate a homo-type fusion. Rab5b is known to exist inside a microvesicle.

As a result, the magnetic beads obtained in (2) above whose protein G was bound to the anti-Rab5b antibody were obtained.

(4) Cross-Linking Between Protein G and Antibody

The bead suspension prepared according to (3) above was washed twice with 400 µl of 0.1 M sodium borate, pH 9.3 buffer. 400 µl of a solution (15 mM dimethyl pimelimidate (DMP) in 0.1 M sodium borate, pH 9.3 buffer) was added to the washed beads and the resultant mixture was rotated for 1 hour. Subsequently, the mixture was washed twice with 400 µl of a solution of 50 mM ethanolamine in a 0.1M sodium borate, pH 8.0 buffer and 200 µl of the same buffer was added thereto, and the resultant mixture was rotated for 1 hour. The reaction product was washed twice with 200 µl of 1× PBS buffer (0.02% Tween 20), washed twice with 200 µl of 1× PBS buffer, and resuspended in 100 µl of 1× PBS buffer.

(5) Binding of the Group of Formula 1 and the Group of Formula 2 or 3 to Surfaces of Magnetic Beads The bead suspension prepared according to (4) above was washed twice with 400 µl of a 0.025 M MES buffer (pH 6.0). Subsequently, 300 µl of a 0.025 M MES buffer (pH 6.0), 50 µl of an EDC solution (75 mg/ml of EDC in 0.025 M MES, pH 6.0), and 50 µl of an NHS solution (15 mg/ml of NHS in 0.025 M MES, pH 6.0) were added to the washed magnetic beads and mixed together, and the resultant mixture was rotated for 30 minutes.

The reacted magnetic beads were washed twice with 400 µl of the same buffer and then resuspended in 400 µl of the same buffer. Then, 6 to 24 µl of Tris (1 mg/µl in D.W.) or 4-aminophenylmethylphosphorylcoline (APC, 1 mg/µl in D.W) was added to the bead suspension and the mixture was rotated for 1 to 2 hours. The reaction product was washed twice with 400 µl of 1× PBS buffer (0.02% Tween 20), washed twice with 400 µl of 1× PBS buffer, and resuspended in 100 µl of 1× PBS buffer. The types of beads synthesized using the method described above are shown in Table 1 below.

TABLE 1

| Bead No. | PAA (µl) | Protein G (µl) | anti-Rab5b antibody (µl) | APC (µl) | Tris (µl) | Remarks |
|---|---|---|---|---|---|---|
| A1 | 65 | 4 | 80 | 0 | 0 | Control |
| A2 | 65 | 8 | 80 | 0 | 0 | |
| B1 | 65 | 4 | 80 | 24 | 0 | Polymer containing at least one repeating unit of Formula M1 where X is APC |
| B2 | 65 | 8 | 80 | 24 | 0 | |
| B3 | 65 | 6 | 80 | 12 | 0 | |
| C1 | 65 | 4 | 80 | 0 | 12 | Polymer containing at least one repeating unit of Formula M1 where X is Tris |
| C2 | 65 | 8 | 80 | 0 | 12 | |
| C3 | 65 | 6 | 80 | 0 | 6 | |

2. Binding Between Polymer and Biomolecules

Binding efficiency of protein Rab5b and binding efficiency of non-specific biomolecules were measured by binding a sample containing protein as biomolecules to the prepared polymer.

(1) Experiment for Binding of Non-Specific Protein

To measure binding efficiency of non-specific protein, the polymer prepared according to 1 above was reacted with a human serum.

First, 200 µl of a mixed solution of human serum (available from Sigma) and 1× PBS buffer was added to 10 µl of prepared magnetic beads and the resultant mixture was rotated at room temperature for 1 hour. Subsequently, a supernatant was removed therefrom and the resultant mixture was washed three times with 200 µl of 1× PBS buffer (0.02% Tween 20). The beads were separated and 60 µl of 1× PBS buffer (2% SDS) was added to the beads and mixed together and then the resultant mixture was incubated at 60° C. for 2 to 3 hours. The solution was then cooled down to room temperature and the amount of protein in the solution was measured using a BCA protein assay kit (available from Pierce). A mixing ratio of human serum and buffer is shown in Table 2 below.

TABLE 2

| Sample name | Serum (%) | buffer and amount (%) |
|---|---|---|
| pH 7.4-S80 | 80 | 1xPBS 20 |
| pH 7.4-S50 | 50 | 1xPBS 20 |
| pH 9.3-S50 | 50 | 0.1M borate 50 |

(2) Measurement of Binding Between Serum and Mixed Specific Protein (2.1) Preparation of Cell Lysate Preparing processes of a cell lysate were all performed in ice or at 4° C. First, a cell pellet was prepared. Breast cancer cell lines, that is, MCF-7 cells, were cultured in a DMEM medium (containing 10% FBS, available from Invitrogen) to a confluency of 70 to 80% (approximately $1.5 \times 10^7$ cells) in 150 mm plate and the medium in the plate was discarded. Thereafter, 10 ml of 1× PBS (pH 7.4) that remained cool was added to the cells. Cells attached to the bottom of the plate were scraped using a scraper and collected and the collected cells were then washed twice with PBS to remove media and residues. The resultant culture was then centrifuged at 300 g for 5 minutes to remove a supernatant (first washing process) and the precipitate (cell pellet) was resuspended with 1 ml of 1× PBS. Next, the cell pellet suspension was placed in 1.7 ml tube and then centrifuged at 1,500 g for 5 minutes to remove a supernatant (second washing process). As a result, a cell pellet was obtained as a cell sample.

A cell lysate was obtained from the cell pellet. A passive lysis solution (available from Promega) having a volume about 5 times that of the cell sample was added to the cell lysate, and the resultant mixture was vortexed three times each for 30 minutes and incubated in ice for 30 minutes, thereby fully lysing the cells. The cell lysate was centrifuged at 12,000 rpm for 30 minutes to remove cell-derived debris and only a supernatant (cell lysate: total protein) was collected and the amount of protein was measured by BCA (available from Pierce) protein assay. The protein was stored at −70° C. prior to use.

(2.2) Binding Between Serum-Containing Cell Lysate and Polymer

200 μl of a mixed solution of human serum (available from Sigma), a buffer, and the cell lysate prepared according to (2.1) above was added to 15 μl of the magnetic beads prepared in (1) above and the mixture was rotated for 1 hour. A liquid portion of the mixture was removed using a magnet and the resultant mixture was washed three times with 200 μl of 1× PBS (0.02% Tween 20), and then the magnetic beads were separated using a magnet. A mixing ratio of serum to buffer to cell lysate is shown in Table 3 below.

TABLE 3

| Sample No. | Serum volume % | Buffer and volume % | Cell lysate volume % |
|---|---|---|---|
| pH7.4-C-S80 | 80 | 0 | 20 |
| pH7.4-C-S50 | 50 | 1×PBS 30 | 20 |
| pH7.4-C-S50 | 50 | 0.1M borate 30 | 20 |

(2.3) Western Blotting

Protein was bound to beads as described in (2.2) above and the beads were added to 7 μl of loading buffer (5 μl LDS sample buffer+2 μl reducing agent, available from Invitrogen) and 13 μl of water. Thereafter, the mixture was heated at 100° C. for 10 minutes to denature protein and the beads with protein bound thereto were separated.

Next, the heated beads were centrifuged and cooled down and each 5 μl of the resultant beads was loaded on SDS-PAGE gels together with a protein size marker (available from Invitrogen) and electrophoresis was conducted by applying 50 mA (constant current) and 200 V for approximately 50 minutes.

After the developing process was terminated, the protein on each gel was transferred to a PVDF membrane at 20 V for 7 minutes 20 seconds by using a dry blotting system (available from Invitrogen). To prevent an antibody from binding to an empty space of the transferred membrane, 10 ml of TBST (1× TBS containing 0.1% Tween 20) buffer containing 5% of powdered skim milk (available from Bio-rad) was added to the membrane and the mixture was maintained for 1 hour to induce a reaction therebetween. After the reaction was terminated, a solution other than the membrane was completely removed. Thereafter, 10 ml of TBST (containing 1% powdered skim milk) containing 5 μl (200 μg/ml) of anti-Rab5b antibody (available from Santacruz Biotechnology) was added to the membrane and maintained at room temperature for 1 hour. After a reaction therebetween incurred, the membrane was washed with 20 ml of distilled water three times each for 5 minutes and a secondary antibody with horseradish peroxidase (HRP) bound thereto and TBST (containing 1% of powdered skim milk) were mixed at a volume ratio of 1:3,000 and the resulting mixture was reacted with the membrane. After the reaction, a washing process was performed using the method described above.

The washed membrane was reacted with 2 ml of SuperSignal West Femto Maximum Sensitivity Support (manufactured by Pierce) at room temperature for 5 minutes, anti-Rab5b bands were detected using LAS (available from Fujifilm) equipment, and detected images were then stored. The intensities of non-specific binding band and anti-Rab5b band in the stored images were each measured using Image J (from NCI) program.

3. Measurement Results (1) Measurement of Binding of Non-Specific Protein

Measurement results of the binding amount of non-specific protein to each of the synthesized beads are shown in Table 4 below. As shown in Table 4, as compared to the beads to which APC or Tris was not bound (A1 and A2 beads), the beads with APC or Tris bound thereto (B1 to B3 beads and C1 to C3 beads) exhibit a reduction in non-specific binding by a maximum of 57%. In addition, the beads with APC bound thereto (B1 to B3) and the beads with Tris bound thereto (C1 to C3) exhibited a similar decrease in non-specific binding.

TABLE 4

| | Binding amount (ng/cm$^2$) | | | Decrease (%)* | | |
|---|---|---|---|---|---|---|
| Bead No. | pH 7.4-S80 | pH 7.4-S50 | pH 9.3-S50 | pH 7.4-S80 | pH 7.4-S50 | pH 9.3-S50 |
| A1 | 1251.9 | 633.9 | 655.4 | 0.0 | 0.0 | 0.0 |
| A2 | 937.7 | 628.9 | 589.1 | 25.1 | 0.8 | 10.1 |
| B1 | 535.4 | 470.2 | 500.2 | 57.2 | 25.8 | 23.7 |
| B2 | 665.1 | 564.6 | 421.1 | 46.9 | 10.9 | 35.7 |
| B3 | 551.4 | 569.4 | 378.0 | 56.0 | 10.2 | 42.3 |
| C1 | 600.4 | 394.8 | 435.3 | 52.0 | 37.7 | 33.6 |
| C2 | 651.3 | 593.0 | 428.3 | 48.0 | 6.5 | 34.7 |
| C3 | 599.2 | 442.9 | 372.4 | 52.1 | 30.1 | 43.2 |

*Decrease (%) is represented by a decrease with respect to A1 beads (2) Measurement Results of Binding of Specific Protein Mixed with Serum FIG. 1 illustrates western blotting results of a polymer with a serum-containing cell lysate bound thereto, according to an embodiment of the present invention.

Referring to FIG. 1, all the beads exhibit similar intensity of bands corresponding to Rab5b protein (lower boxes), while exhibiting different intensity of bands corresponding to protein by non-specific binding (upper boxes). Such a difference is attributed to whether or not the polymer including the repeating units of Formulae M1 and M2 where X and Y are each independently a group having at least two terminal hydroxyls or a zwitterionic group is bound to the beads. In other words, as compared to the beads not including the polymer (A1 and A2 beads), the beads with the polymer bound thereto (B1 to B3 and C1 to C3) exhibited a lower intensity of bands by non-specific binding. The beads with APC bound thereto (B1 to B3) and the beads with Tris bound thereto (C1 to C3) exhibited a similar intensity of bands by non-specific binding. The measurement results of the intensity of bands of FIG. 1 are shown in Table 5 below.

TABLE 5

| Bead No. | Band intensity of specific protein | | | Band intensity of non-specific protein | | |
|---|---|---|---|---|---|---|
| | pH 7.4-C-S80 | pH 7.4-C-S50 | pH 9.3-C-S50 | pH 7.4-C-S80 | pH 7.4-C-S50 | pH 9.3-C-S50 |
| A1 | 107.0 | 105.9 | 96.5 | 56.5 | 67.6 | 54.9 |
| A2 | 97.7 | 96.9 | 84.7 | 36.9 | 43.2 | 34.6 |
| B1 | 91.1 | 91.0 | 84.1 | 29.6 | 43.7 | 31.5 |
| B2 | 88.7 | 79.2 | 74.7 | 28.0 | 36.5 | 24.8 |
| B3 | 96.0 | 89.5 | 87.7 | 30.4 | 36.5 | 33.1 |
| C1 | 103.5 | 104.3 | 98.3 | 14.7 | 17.8 | 16.2 |
| C2 | 90.9 | 87.8 | 79.0 | 29.0 | 31.8 | 24.0 |
| C3 | 89.6 | 89.8 | 89.4 | 28.9 | 34.3 | 30.5 |

As shown in Table 5, as anticipated from FIG. 1, while a difference in band intensities of specific protein of all the beads is less than 10%, A1 and A2 beads show a big difference in the intensity of bands by non-specific protein as compared to the beads with APC bound thereto (B1 to B3) and the beads with Tris bound thereto (C1 to C3). In particular, the band intensity of the beads with APC bound thereto (B1 to B3) and the beads with Tris bound thereto (C1 to C3) is less intense as compared to that of A1 and A2 beads. In addition, although the band intensities vary according to types of a sample, the beads with APC bound thereto and the beads with Tris bound thereto exhibit similar band intensities.

Example 2

Preparation of Polymer and Binding of Biomolecules Thereto

1. Synthesis of Polymer

PAA including the repeating units of Formulae M1 and M2 where X and Y are each independently —H, A is —O—, $R_1$ and $R_4$ are each independently —CH$_2$—, $R_2$ and $R_5$ are each independently —H, and $R_3$ and $R_6$ are each independently a single bond (—) was prepared as a polymer and the polymer was bound to a surface of a solid support. Subsequently, a carboxyl group of PAA was activated using carbodiimide and the activated carboxyl group was reacted with amino groups of the groups of Formulae 1, 3, and 4 and an amino group of biomolecules (e.g., protein) to immobilize the groups of Formulae 1, 3, and 4, wherein the group of Formula 1 has an amino group functionalized with at least one hydroxyl site, for example, a hydroxyl group at the end and the biomolecules (e.g., protein) on the solid support. Beads were used as the solid support. The preparation of the polymer will now be described in more detail.

(1) Binding of First Polymer Having Carboxyl Group to Magnetic Beads

Magnetic beads were used as a solid support. Dynabeads® M-270 Amine (available from Invitrogen) were used. Dynabeads® M-270 Amine are uniform, superparamagnetic beads composed of highly cross-linked polystyrene with magnetic material precipitated in pores evenly distributed throughout the beads. The beads are further coated with a hydrophilic layer of glycidyl ether which seals the iron oxide inside the beads, and the surface is activated with primary amino functionality on a short hydrophilic linker.

The hydrophilic surface ensures low non-specific binding, excellent dispersion abilities and easy handing of the beads in a wide variety of buffers. The beads are sold in an aqueous suspension at a concentration of $2 \times 10^9$ beads/ml (approx. 30 mg/ml). The diameter of the magnetic beads was 2.8 µm. Surface-reactive primary amino groups allow immobilization of ligands such as proteins, peptides, carbohydrates or other target specific molecules.

100 µl of Dynabeads® M-270 Amine (available from Invitrogen) was washed twice with 200 µl of 0.1M MES, 0.5 M NaCl, pH 6 buffer and then resuspended in 100 µl of the same buffer. 48 µl of a 1:10 diluted solution of a PAA solution (35% w/v in water, average molecular weight ($M_w$) of about 15,000 Da, catalog No.: 416037, available from Aldrich) and 236 µl of the buffer were mixed together and the resultant mixture was added to the resuspended bead solution and mixed well.

Next, 54 µl of a solution in which 75 mg/ml of EDC is dissolved in distilled water and 210 µl of a solution in which 15 mg/ml of NHS is dissolved in distilled water were added to the mixture and the resulting mixture was rotated for 1 hour. Subsequently, the mixture was washed twice with 400 µl of a 0.5M NaCl, pH 6.0 buffer and resuspended in 400 µl of the same buffer. As a result, magnetic beads with PAA bound to the surfaces by an amide bond were obtained. The amide bond was formed by binding between a carbonyl group of PAA and primary amino groups of the magnetic beads.

(2) Binding of Protein G and Blocker to Magnetic Beads with PAA Bound to the Surfaces The bead suspension prepared according to (1) was washed twice with 400 µl of 0.025 M MES buffer (pH 6.0). Subsequently, 236 µl of the same buffer, 54 µl of an EDC solution (75 mg/ml EDC in 0.025 M MES, pH 6.0 buffer), and 210 µl of an NHS solution (15 mg/ml of NHS in 0.025 M MES, pH 6.0 buffer) were added to the resultant bead suspension and mixed together, and the resultant mixture was then rotated for 30 minutes.

The magnetic beads were washed twice with 400 µl of the same buffer and resuspended in 400 µl of the same buffer. Then, 3 µl of a protein G solution (10 µg/µl) (available from Fluka, catalog No.: 08062) was added to the bead suspension and the resultant mixture was rotated for 1 hour. As a result, magnetic beads having PAA with protein G bound thereto on their surfaces were obtained. In this regard, protein G may be bound to the magnetic beads via a carbonyl group of PAA.

Next, according to the type of blockers to be used in the reaction product, each blocker was added to the reaction product to couple the blocker with a backbone of the PAA. In particular, each of 28 µl of a Tris solution (100 µg/µl of Tris in distilled water), 50 µl of an APC solution (100 µg/µl of APC in distilled water), 300 µl of a SB solution (100 µg/µl of SB ($NH_2(CH_2)_3N^+(CH_3)_2(CH_2)_3SO_3^-$) in distilled water), and 300 µl of a PEG solution (20 µg/µl of PEG (BlockMaster, JSR corporation: Mw=5,000 Da) in distilled water) was added to the reaction product and each mixture was rotated for 1 to 2 hours. Each reaction product was washed twice with 400 µl of 1× PBS (0.02% Tween 20) and washed twice with 400 µl of 1× PBS. In this regard, PEG whose terminal OH group is functionalized to an amino group was used. That is, the used PEG was a synthetic aqueous polymer with amine (—NH$_2$) group at one end.

(3) Binding Between Protein G and Antibody

Magnetic beads were separated from the bead suspension prepared according to (2) above by using a magnet and the magnetic beads were washed twice with 400 µl of 0.1M sodium acetate buffer (pH 5.0).

160 µl of anti-EpCAM antibody (available from R&D system: p9601, 0.5 µg/µl) and 340 µl of 0.1M sodium acetate buffer (pH 5.0) were mixed together, the mixture was added to the washed magnetic beads, and the resulting mixture was rotated for 3 hours. The reaction product was washed twice with 200 µl of 1× PBS (0.02% Tween 20), washed twice with 200 µl of 1× PBS, and then resuspended in 100 µl of 1× PBS.

In humans, epithelial cell adhesion molecules (EpCAMs) are proteins encoded by an EpCAM gene. EpCAM is a pan-epithelial differentiation antigen that is expressed on almost all carcinomas. EpCAM is expressed in undifferentiated pluripotent stem cells.

As a result, the magnetic beads prepared according to (2) above whose protein G is bound to anti-EpCAM antibody was obtained. In this regard, protein G is considered to be non-covalently bound to anti-EpCAM antibody.

(4) Cross-Linking of Protein G and Antibody

The bead suspension prepared according to (3) above was washed twice with 400 µl of 0.1M sodium borate buffer (pH 9.3). Subsequently, 400 µl of a solution of 15 mM dimethyl pimelimidate (DMP) in 0.1M sodium borate buffer, pH 9.3 was added to the washed magnetic beads and the mixture was rotated for 1 hour. Thereafter, the reaction product was washed twice with 400 µl of a solution of 50 mM ethanol amine in 0.1M sodium borate buffer (pH 8.0), 200 µl of the same buffer was added to the reaction product, and the resulting mixture was rotated for 1 hour. The reaction product was washed twice with 200 µl of 1× PBS (0.02% Tween 20), washed twice with 200 µl of 1× PBS, and then resuspended in 100 µl of 1× PBS.

TABLE 6

| Bead No. | PAA (µl) | Protein G (µl) | Anti-EpCAM antibody (µl) | blocker | Remarks |
|---|---|---|---|---|---|
| 2-1 | 48 | 3 | 160 | 0 | Control not including blocker |
| 2-2 | 48 | 3 | 160 | Tris | |
| 2-3 | 48 | 3 | 160 | APC | |
| 2-4 | 48 | 3 | 160 | SB | |
| 2-5 | 48 | 3 | 160 | PEG | |

2. Binding Between Polymer and Biomolecules

Binding efficiency of protein EpCAM and binding efficiency of non-specific biomolecules were measured by binding a sample containing protein as biomolecules to the prepared polymer.

(1) Experiment for Binding of Non-Specific Protein

To measure binding efficiency of non-specific protein, the polymer prepared according to 1 above was reacted with a human serum.

First, 200 µl of a mixed solution of human serum (available from Sigma) and 1× PBS buffer was added to 20 µl of prepared magnetic beads and the resultant mixture was rotated at room temperature overnight. Subsequently, a supernatant was removed therefrom and the resultant mixture was washed three times with 200 µl of 1× PBS buffer (0.02% Tween 20). The beads were separated and 90 µl of 1× PBS buffer (2% SDS) was added to the beads and mixed together and then the resultant mixture was incubated at 60° C. for 2 to 3 hours. The solution was then cooled down to room temperature and the amount of protein in the solution was measured using a BCA protein assay kit (available from Pierce). A mixing ratio of human serum to buffer (1× PBS) was 9:1.

(2) Measurement of Binding of Target Protein on Surface of Microvesicle in Serum (2.1) Preparation of Exosome Pellet Exosome was used as a microvesicle. Preparing processes of exosome were all performed in ice or at 4° C. Breast cancer cell lines, that is, MCF-7 cells, were cultured in a DMEM medium (containing 10% FBS, available from Invitrogen) to a confluency of 70 to 80% (approximately $1.5 \times 10^7$ cells) in 150 mm plate and the medium was collected using a 50 ml centrifugal separation tube. Subsequently, the 50 ml centrifugal separation tube was centrifuged at 300 g at 4° C. for 10 minutes to obtain a supernatant. The supernatant was then placed in a new centrifugal separation tube and the centrifugal separation tube was centrifuged at 800 g at 4° C. for 10 minutes to obtain a supernatant. Next, the supernatant was placed in a new centrifugal separation tube and the centrifugal separation tube was centrifuged at 2,000 g at 4° C. for 20 minutes to obtain a supernatant. The supernatant was then placed in a polycarbonate tube and centrifuged at 10,000 g at 4° C. for 30 minutes. The obtained supernatant was then placed in a polycarbonate tube and centrifuged at 110,000 g at 4° C. for 70 minutes. The obtained supernatant was completely removed, and the obtained pellet was resuspended in 1 ml of PBS and centrifuged at 100,000 g at 4° C. for 70 minutes. The obtained supernatant was completely removed. The amount of protein in the pellet was measured using a BCA protein assay kit (available from Pierce) and the pellet was stored at −70° C. before use.

(2.2) Binding Between Target Protein on Surface of Exosome and Polymer

200 µl of a mixed solution of human serum (available from Sigma), a buffer, and the solution containing exosome prepared according to (2.1) above was added to 20 µl of the magnetic beads prepared according to (1) above and the mixture was rotated for 1 hour. A liquid portion of the mixture was removed using a magnet and the resultant mixture was washed three times with 200 µl of 1× PBS (0.02% Tween 20), and then the magnetic beads were separated using a magnet. In this regard, a mixing ratio of serum to buffer to exosome was 180:18:2.

(2.3) Western Blotting

Protein was bound to the beads prepared according to (2.2) above and the beads were added to 7 µl of loading buffer (5 µl LDS sample buffer+2 µl reducing agent, available from Invitrogen) and 13 µl of water. Thereafter, the mixture was heated at 100° C. for 10 minutes to denature protein and the beads with protein bound thereto were separated.

Next, the heated beads were centrifuged and cooled down and each 5 µl of the resultant beads was loaded on SDS-PAGE gels together with a protein size marker (available from Invitrogen) and each gel was developed for approximately 50 minutes at 100 mA and 200 V.

After the developing process was terminated, the protein on each gel was transferred to a PVDF membrane at 20 V for 7 minutes 20 seconds by using a dry blotting system (available from Invitrogen). To prevent an antibody from binding to an empty space of the transferred membrane, 10 ml of TBST (1× TBS containing 0.1% Tween 20) buffer containing 5% of powdered skim milk (available from Bio-rad) was added to the membrane and the mixture was maintained for 1 hour to induce a reaction therebetween. After the reaction was terminated, a solution other than the membrane was completely removed. Thereafter, 10 ml of TBST (containing 1% powdered skim milk) containing 1 µl (200 µg/ml) of anti-EpCAM antibody (available from R&D systems) was added to the membrane and maintained at room temperature for 1 hour. After a reaction therebetween incurred, the membrane was washed with 20 ml of distilled water three times each for 5 minutes and 10 ml of TBST (containing 1% powdered skim milk) containing 1 μl (200 μg/ml) of a secondary antibody with horseradish peroxidase (HRP) bound thereto was added to the membrane and maintained at room temperature for 1 hour. After the reaction, a washing process was performed using the method described above.

The washed membrane was reacted with 2 ml of SuperSignal West Femto Maximum Sensitivity Support (manufactured by Pierce) at room temperature for 5 minutes, anti-EpCAM bands were detected using LAS (available from Fujifilm) equipment, and detected images were then stored. The intensities of non-specific binding band and anti-EpCAM band in the stored images were each measured using Image J (from NCI) program.

3. Measurement Results (1) Measurement of Binding of Non-Specific Protein

Measurement results of the binding amount of non-specific protein to each of the synthesized beads are shown in Table 7 below. As shown in Table 7, as compared to the beads to which a blocker was not bound (2-1 beads), the beads with a blocker bound thereto (2-2, 2-3, 2-4 and 2-5 beads) exhibit a significant reduction in binding of non-specific protein. In particular, with respect to the 2-1 beads, the binding amounts of non-specific protein of the 2-2, 2-3, 2-4 and 2-5 beads were 60%, 66%, 33%, and 41%, respectively. In other words, the binding amounts of non-specific protein of the 2-3 and 2-4 beads were reduced by 34% and 67%, respectively as compared to that of the 2-1 beads. The values shown in Table 7 are average values.

TABLE 7

| Bead No. | Binding amount of protein | Decrease (%)* |
|---|---|---|
| 2-1 | 5210.9 | 0 |
| 2-2 | 3131.0 | 40 |
| 2-3 | 3462.2 | 34 |
| 2-4 | 1745.0 | 67 |
| 2-5 | 2162.3 | 59 |

Figure 2:
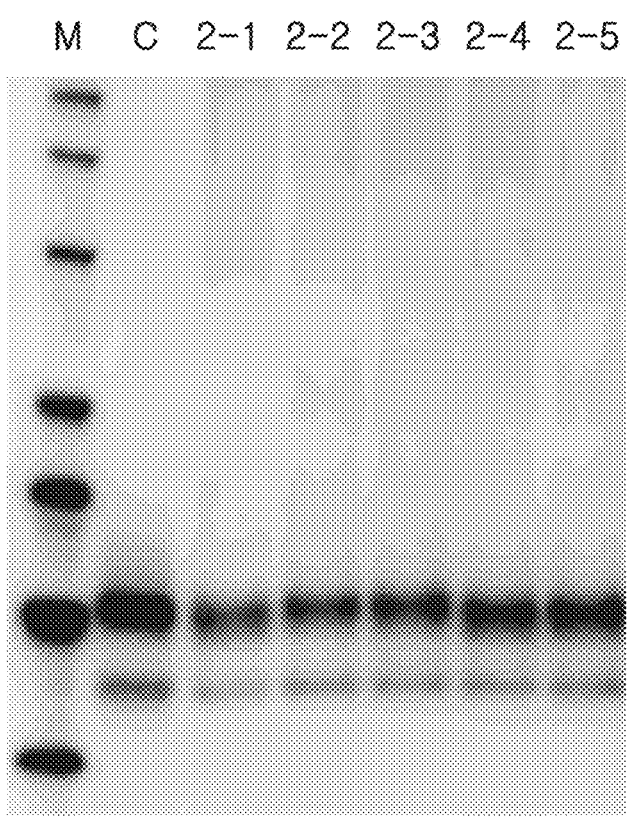
FIG. 2 illustrates western blotting results of a polymer to which an exosome solution containing a serum is bound, according to an embodiment of the present invention.

*Decrease (%) is represented by a decrease with respect to 2-1 beads (2) Measurement Results of Binding of Target Protein on Surface of Exosome FIG. 2 illustrates western blotting results of a polymer to which an exosome solution containing a serum is bound. The measurement results of the intensities of bands corresponding to EpCAM of FIG. 2 are shown in Table 8 below. In FIG. 2, M denotes a molecular weight marker and C indicates a case in which a target protein is injected. The values shown in Table 8 are average values.

TABLE 8

| Bead No. | Intensity | Capture efficiency (%)* |
|---|---|---|
| 2-1 | 86.3 | 100 |
| 2-2 | 88.1 | 102 |
| 2-3 | 100.1 | 116 |
| 2-4 | 111.8 | 130 |
| 2-5 | 111.2 | 129 |

*Capture efficiency (%) is represented by percentage with respect to 2-1 beads

As shown in Table 8, the capture efficiencies of specific protein on a surface of exosome or exosome of the 2-2, 2-3, 2-4 and 2-5 beads that contain a blocker are increased by 2%, 16%, 30%, and 29%, respectively, with respect to the 2-1 beads. This indicates that the beads including a blocker not only decrease non-specific binding of protein but also increase the capture efficiency of a target protein or a microvesicle with a target protein on the surface. In particular, this indicates that the beads including sulfobetaine as a blocker not only decrease non-specific binding of protein but also increase the capture efficiency of a target protein or a microvesicle with a target protein on the surface.

From the results described above, it is confirmed that, when both a blocker that blocks non-specific binding of protein and a binding moiety that binds to target molecules are attached to a polymer immobilized on a solid support, unexpected effects such as efficient separation of target molecules in a sample are obtained. In particular, it is confirmed that, when target molecules exist on a surface of a microvesicle, the microvesicle may be captured using binding affinity between binding molecules and the target molecule, and the target molecules may be efficiently separated therefrom.

As described above, according to the one or more embodiments of the present invention, by using the polymer described above, specific biomolecules may be specifically bound to the polymer without binding of non-specific biomolecules, for example, protein.

By using the method described above, specific biomolecules may be specifically bound to the polymer without binding of non-specific biomolecules, for example, protein thereto. Also, a material containing specific biomolecules, for example, a cell or a microvesicle may be specifically bound to the polymer by the specific binding between the specific biomolecules and the polymer.

By the method described above, specific biomolecules may be separated from a sample without binding of non-specific biomolecules, for example, protein. In addition, a material containing specific biomolecules, for example, a cell or a microvesicle may be specifically separated from a sample by specific binding between the specific biomolecules and the polymer and separation of the specific biomolecules therefrom.

By using the method described above, it may be efficiently detected whether or not biomolecules exist in the sample.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A solid support on which at least one polymer comprising at least one repeating unit of Formula M1 and at least one repeating unit of Formula M2 is immobilized:

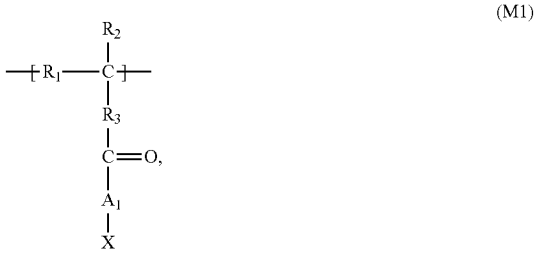

-continued

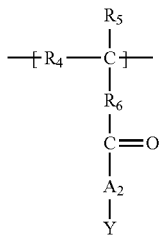

wherein $R_1$, $R_3$, $R_4$, and $R_6$ are each independently a bond or a substituted or unsubstituted $C_{1-6}$ alkylene group, $R_2$ and $R_5$ are each independently hydrogen, halo, or a substituted or unsubstituted $C_{1-6}$ alkyl group, $A_1$ and $A_2$ are each independently —NH—, —O—, or —O—(CO)—, and wherein $R_7$ is a substituted or unsubstituted $C_{1-6}$ alkylene group, a substituted or unsubstituted $C_{6-12}$ arylene group, a substituted or unsubstituted $C_{1-6}$ alkyl-$C_{6-12}$ arylene group, or a substituted or unsubstituted $C_{6-12}$ aryl-$C_{1-6}$ alkylene group;

and $R_8$, $R_9$, and $R_{10}$ are each independently H, halo, or a substituted or unsubstituted $C_{1-6}$ hydroxyalkyl group, wherein at least two of $R_8$, $R_9$, and $R_{10}$ are each independently a substituted or unsubstituted $C_{1-6}$ hydroxyalkyl group wherein the zwitterionic group is represented by Formula 2 below:

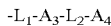  <Formula 2> wherein $L_1$ and $L_2$ are each independently a substituted or unsubstituted $C_{1-100}$ alkylene group, a substituted or unsubstituted $C_{6-100}$ arylene group, a substituted or unsubstituted $C_{1-50}$ alkyl-$C_{6-50}$ arylene group, or a substituted or unsubstituted $C_{6-50}$ aryl-$C_{1-50}$ alkylene group;

and $A_3$ and $A_4$ are ionic groups, wherein $A_3$ is a cationic group and $A_4$ is an anionic group; or $A_3$ is a anionic group and $A_4$ is an cationic group, and wherein the material that specifically binds to one or more biomolecules is an antibody, an antigen, a receptor, a ligand, a substrate or inhibitor of an enzyme, or an enzyme, wherein M1 and M2 are different, wherein 10% to 90% of the repeating units of the polymer comprises at least one material that specifically binds to one or more biomolecules, wherein 10% to 90% of the repeating units of the polymer comprises a group having at least two hydroxyls, a zwitterionic group, PEG, or a combination thereof, and wherein the number of the repeating units of Formula M1 of the polymer is an integer of 1 to 300 and the number of the repeating units of Formula M2 of the polymer is an integer of 1 to 300, and wherein X is a group having at least two hydroxyls represented by Formula 1

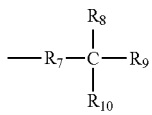  <Formula 1> and Y is a material that specifically binds to one or more biomolecules.

2. The solid support of claim 1, wherein at least one of $R_1$, $R_2$, $R_3$, $R_4$, $R_5$, and $R_6$ is a $C_{1-6}$ alkyl group substituted with one or more halo or $C_{1-3}$ alkyl groups.

3. The solid support of claim 1, wherein at least one of $R_7$, $R_8$, $R_9$, and $R_{10}$ is further substituted with one or more halo or $C_{1-3}$ alkyl groups.

4. The solid support of claim 1, wherein the material that specifically binds to one or more biomolecules is an antibody that binds to a protein of a microvesicle membrane.

5. The solid support of claim 1, wherein the solid support is a bead, a plate, or a well.

6. The solid support of claim 1, wherein the polymer further comprises a portion bonded to the solid support, which portion of the polymer comprises units of formula M1, M2, or both:

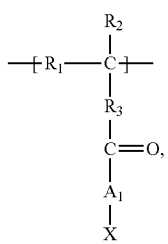

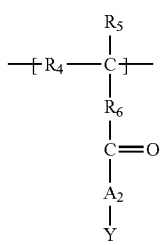

wherein $R_1$ and $R_4$ are each independently —$CH_2$—;
$R_3$ and $R_6$ are each independently a single bond;
$R_2$ and $R_5$ are each independently —H; and
$A_1$ and $A_2$ are each independently —NH—.

7. A method of binding biomolecules from a sample to a solid support, the method comprising contacting a solid support of claim 1 with biomolecules from a sample to form a biomolecule-solid support composite.

8. The method of claim 7, further comprising washing the biomolecule-solid support composite after contacting the support with the biomolecules.

9. The method of claim 7, further comprising eluting biomolecules from the biomolecule-solid support composite after contacting the support with the biomolecules.

10. A method of preparing a solid support according to claim 1, the method comprising:

providing a polymer comprising repeating units of Formula M1 and Formula M2:

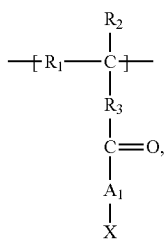

-continued

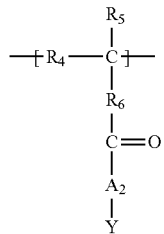
(M2)

wherein $R_1$, $R_3$, $R_4$, and $R_6$ are each independently a bond or a substituted or unsubstituted $C_{1-6}$ alkylene group,
$R_2$ and $R_5$ are each independently hydrogen, halo, or a substituted or unsubstituted $C_{1-6}$ alkyl group,
$A_1$ and $A_2$ are each independently —O—;

and X and Y are both H;
coupling the carboxyl group provided by A1 and X with a group having at least two hydroxyls represented by Formula 1

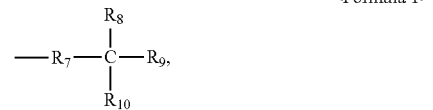
<Formula 1> and coupling the carboxyl group provided by A2 and Y, with a material that specifically binds to one or more biomolecules;
and immobilizing the polymer on a solid support.

* * * * *